United States Patent
Norman et al.

(10) Patent No.: US 8,969,632 B2
(45) Date of Patent: Mar. 3, 2015

(54) PASSIVATION OF A HOMOGENEOUS HYDROGENATION CATALYST FOR THE PRODUCTION OF ETHYLENE GLYCOL

(75) Inventors: David William Norman, Kingsport, TN (US); Jonathan Michael Penney, Gray, TN (US); Peter Borden Mackenzie, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 608 days.

(21) Appl. No.: 13/428,333

(22) Filed: Mar. 23, 2012

(65) Prior Publication Data

US 2013/0253230 A1 Sep. 26, 2013

(51) Int. Cl.
*C07C 29/149* (2006.01)
*C07C 29/141* (2006.01)
*C07C 29/145* (2006.01)

(52) U.S. Cl.
USPC .................. 568/864; 568/862; 568/863

(58) Field of Classification Search
CPC .... C07C 29/149; C07C 29/141; C07C 29/145
USPC ......................................... 568/864, 862, 863
See application file for complete search history.

(56) References Cited

U.S. PATENT DOCUMENTS

| | | | |
|---|---|---|---|
| 2,152,852 | A | 4/1939 | Loder et al. |
| 2,153,064 | A | 4/1939 | Larson |
| 2,211,624 | A | 8/1940 | Loder et al. |
| 2,211,625 | A | 8/1940 | Loder et al. |
| 3,948,977 | A | 4/1976 | Suzuki |
| 7,615,671 | B2 | 11/2009 | Puckette et al. |
| 7,709,689 | B2 | 5/2010 | Kilner et al. |
| 7,763,758 | B2 | 7/2010 | Saudan et al. |
| 2009/0143612 | A1 | 6/2009 | Puckette et al. |
| 2010/0099550 | A1 | 4/2010 | Kilner et al. |
| 2012/0046481 | A1 | 2/2012 | Barnicki et al. |
| 2012/0046500 | A1 | 2/2012 | Barnicki et al. |

FOREIGN PATENT DOCUMENTS

GB 1499245 A 1/1978

OTHER PUBLICATIONS

Osborn, J. A., et al., "The Preparation and Properties of Tris(triphenylphosphine)halogenorhodium(i) and Some Reactions thereof including Catalytic Homogeneous Hydrogenation of Olefins and Acetylenes and their Derivatives", Journal of the Chemical Society (A), 1966, pp. 1711-1732.
Clarke, Zaheer E., "A Family of Active Iridium Catalysts for Transfer Hydrogenation of Ketones", Organometallics, 2006, 25, pp. 4113-4117.
Mitchell, Robert. W., et al., "Carboxylato-triphenylphosphine Complexes of Ruthenium, Cationic Triphenylphosphine Complexes derived from them, and their Behavior as Homogeneous Hydrogenation Catalysts for Alkenes", Journal of the Chemical Society, Dalton Trans., 1973, pp. 846-854.
Robinson, Stephen. D, et al., "Complexes of the Platinum Metals. Part II. Carboxylato(triphenylphosphine) Derivatives of Ruthenium, Osmium, Rhodium, and Iridium", Journal of the Chemical Society. Dalton Trans., 1973, pp. 1912-1920.
Lynam, Jason, et al., "Exploitation of a Chemically Non-innocent Acetate Ligand in the Synthesis and Reactivity of Ruthenium Vinylidene Complexes", Organometallics, 2009, vol. 28, pp. 1320-1328.
Hommeltoft, Sven. I. et al., "Oxidative Addition Reactions of Dicarbonyl[1,1,1-tris((diphenylphosphino)methyl)ethane]ruthenium(0). Elimination of Ketene from an Acetylmetal Compound", Organometallics, 1986, vol. 5, issue 2, pp. 190-195.
Siegl, W. O., et al., "Ruthenium(0) and Ruthenium (II) Complexes with 1,1,1-Tris(diphenylphosphinomethyl)ethane", Inorganic Chemistry, 1973, vol. 12, No. 3, pp. 674-677.
Kitamura, M., et al., "Homogeneous Asymmetric Hydrogenation of Functionalized Ketones", Journal of American Chemical Society, 1988, vol. 110, No. 2, pp. 629-631.
Zhang, Jing, et al., "Efficient Homogeneous Catalytic Hydrogenation of Esters to Alcohols", Angewandte Chemie Int. Ed., 2006, 45, pp. 1113-1115.
Notification of Transmittal of The International Search Report and The Written Opinion of the International Searching Authority, or the Declaration; International Application No. PCT/US2013/029773 with a mailing date of Jun. 19, 2013.
Watanabe, Eiichi, et al.; "A novel rhodium-tri-N-alkylphosphine catalyst system for the hydrogenation of carbon monoxide, formaldehyde, and glycolaldehyde"; Chemistry Letters, (1986), pp. 285-288.

*Primary Examiner* — Elvis O Price
(74) *Attorney, Agent, or Firm* — Dennis V. Carmen

(57) ABSTRACT

A process for making ethylene glycol by feeding reactants including 1,2-dioxygenated organic compounds, an organometallic homogeneous catalyst, and hydrogen to a hydrogenation reactor, reacting at least a portion of the reactants with hydrogen in the presence of the organometallic homogeneous catalyst to produce a reaction product mixture containing ethylene glycol, and passivating the catalyst by contacting the catalyst with a carbon monoxide to thereby suppress the formation of by-product diols other that the ethylene glycol primary product, and suppress the formation of by-product tetrols and by-product glycolaldehyde acetals; and separating at least a portion of the ethylene glycol from the reaction product mixture.

23 Claims, No Drawings

PASSIVATION OF A HOMOGENEOUS HYDROGENATION CATALYST FOR THE PRODUCTION OF ETHYLENE GLYCOL

1. FIELD OF THE INVENTION

The present invention relates to formation of a reaction product mixture containing ethylene glycol by hydrogenating a 1,2-dioxygenated organic compound with hydrogen in the presence of a homogeneous organometallic catalyst and suppressing the formation of additional organic by-products formed after hydrogenation by passivating the homogeneous catalyst with carbon monoxide.

2. BACKGROUND OF THE INVENTION

The conventional process for preparing monoethylene glycol (EG) entails partial oxidation of ethylene followed by hydration of the resulting oxide. Hydrogenation of glycolic acid and its esters (hereafter collectively referred to as glycolates or glycolate esters) is a substitute technology for producing EG.

Homogeneous ruthenium complexes bearing the tripodal phosphine ligand 1,1,1-tris-(diphenylphosphinomethyl) ethane, commonly known as 'Triphos', are known to reduce glycolate esters under elevated temperature and hydrogen pressure. Since these complexes are thermally stable, product purification by distillation followed by recycle of the resulting catalyst enriched heel would provide a process cost savings. One consequence of this approach, however, is the ruthenium catalyzed degradation of the ethylene glycol. Indeed, according to the principal of microscopic reversibility, a hydrogenation catalyst is also capable of dehydrogenation, particularly under non-reducing atmospheres.

Dehydrogenation of ethylene glycol produces hydrogen and an equivalent molar amount of glycolaldehyde which, in the presence of excess EG, forms mono- and di-EG acetals (hereafter referred to as 'glycolaldehyde acetals' or 'glycolaldehydes'). Butane tetra-alcohol byproducts such as threitol and erythritol (hereafter collectively referred to as 'by-product tetrols') are believed to form from these glycolaldehydes. These by-product tetrols can decompose into other byproducts such as 1,2-butanediol and 1,2-propanediol (hereafter collectively referred to as 'by-product diols').

There exist downstream locations where the reaction mixture is under non-reducing atmospheres and additional by-products can form, such as in heat trace lines leading to a distillation column, and in the purification section (a distillation column itself) that is used to separate EG from the reaction mixture effluent of the hydrogenation reactor. The concentration of these by-products, particularly that of the by-product diols, can be problematic during product purification, especially in separation via distillation. The by-product diols in particular will tend to travel with EG as an overhead vapor, thereby reducing the purity of the EG overhead. While the separation of EG from by-product tetrols and by-product glycolaldehyde species is easier to separate than EG from diols, the formation of any by-products while the effluent from the hydrogenation reactor is in route to the purification section, or their formation in the distillation column, represents a yield loss in EG and variability in EG yield. This is also undesirable in a commercial hydrogenation/purification EG process.

We have found that dehydrogenation or degradation reactions of ethylene glycol can also occur in a reducing atmosphere to form by-products such as diols other than ethylene glycol, by-product tetrols, and by-product glycolaldehyde species. Even under hydrogenation conditions, the EG being formed can be subjected to dehydrogenation to produce by-products. During hydrogenation in the hydrogenation reactor, one can control the amount of by-product formation in the hydrogenation reactor through temperature, pressure, degree of conversion, and activity of the catalyst and one can also account for the number of moles of diols produced during the hydrogenation step. However, the formation of by-products after the hydrogenation step is problematic because the formation of these additional by-product diols are difficult to account for, which adds to variability and reduced control of the process, and also adds to the quantity of by-products already present in the hydrogenation reactor and yield loss of EG. Thus, minimizing all by-product formation downstream of the hydrogenation reactor, and especially by-product diol formation, and minimizing variability in the compositional mixture after discharging the effluent from the hydrogenation reactor would clearly benefit a commercial application of a hydrogenation/purification EG process.

3. SUMMARY OF THE INVENTION

There is now provided a process for suppressing the formation of diol by-products in the presence of a hydrogenation catalyst. Heating a hydrogenation reactor effluent containing ethylene glycol and a homogeneous organometallic catalyst under a carbon monoxide gas atmosphere suppresses by-product diol (other than ethylene glycol) by-product formation. In many instances, the formation of by-product tetrols and by-product glycolaldehydes can also be suppressed, but even if not, these by-products can be separated easier than diol by-products can be separated from the ethylene glycol product, thereby obtaining a more consistent and higher ethylene glycol purity in the overhead stream.

There is now provided a process for making ethylene glycol comprising:
  (i) feeding reactants comprising 1,2-dioxygenated organic compounds, an organometallic homogeneous catalyst, and hydrogen to a hydrogenation reactor;
  (ii) conducting a hydrogenation reaction by reacting at least a portion of the reactants with hydrogen in the hydrogenation reactor and in the presence of the catalyst to produce a reaction product mixture comprising ethylene glycol and the catalyst;
  (iii) contacting the catalyst with a carbon monoxide gas composition containing at least 1 mole % carbon monoxide; and
  (iv) separating at least a portion of the ethylene glycol from the reaction product mixture.

The reaction product mixture is contacted with a carbon monoxide gas composition, and the cumulative supplemental amount of 1,2-propanediol and 1,2-butanediol formed as diol by-products after first contact with said carbon monoxide gas composition is reduced relative to a reaction product mixture which is not contacted with the carbon monoxide gas composition.

The reaction product mixture is contacted with carbon monoxide gas composition, and the cumulative supplemental amount of by-product tetrols formed as tetrols by-products after first contact with said carbon monoxide gas composition is reduced relative to a reaction product mixture that is not exposed to the carbon monoxide gas composition.

The reaction product mixture is contacted with carbon monoxide gas composition, and the cumulative supplemental amount of glycolaldehyde acetal compounds formed as acetal by-products after first contact with said carbon monoxide gas composition can be reduced relative to a reaction product mixture which is not exposed to the carbon monoxide gas.

4. DETAILED DESCRIPTION OF THE INVENTION

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range and their endpoint(s). For example, a range stated to be from 0 to 10 is intended to disclose all whole numbers from 0 and 10 such as, for example 0, 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

All percentages are by mole unless otherwise stated.

As used herein, "by-products" means 1,2-propanediol, 1,2-butanediol, erythritol, threitol, glycolaldehyde acetals, or a combination of any two or more of the foregoing compounds.

"By-product diol(s)" means 1,2-propanediol, 1,2-butanediol, or a combination thereof.

"By-product tetrols(s)" means erythritol, threitol, or a combination thereof.

"By-product glycolaldehyde acetal(s)" means one or more of the reaction products of ethylene glycol with glycolaldehyde.

A reactant composition is fed to the hydrogenation reactor. The reactants are 1,2-dioxygenated organic compounds. 1,2-Dioxygenated organic compounds are organic compounds in which adjacent carbon atoms are bonded to one or more oxygen atoms and in which there is a double bond between at least one of the adjacent carbon atoms and its oxygen substituent. For example, the adjacent carbon atoms each may be part of an aldehyde, carbonyloxy, ester, or hydroxyl group as long as one of them has a double bond to an oxygen atom. Representative classes of 1,2-dioxygenated organic compounds include, but are not limited to, α-hydroxyalkanoic acids and esters thereof, α-hydroxyaldehydes, α-formylcarboxylic acids and esters and acetals thereof, and glyoxaldehyde and acetals thereof. The term "esters thereof", in the context of the above list of compounds, means an ester formed by the reaction of a carboxylic acid with the hydroxy group, by the reaction of alcohols with the carboxylic acid group, or a combination thereof, and polymeric or oligomeric esters formed by the condensation of 2 or more α-hydroxyalkanoic acid molecules.

Examples of 1,2-dioxygenated organic compounds suitable for hydrogenation in the process of the invention include glyoxal, glycolic acid, glycolaldehyde, glycolaldehyde dimer, glycolic acid mono or di-esters, methyl glycolate, oligomers of glycolic acid, oligomers of glycolic acid esters, oxalic acid, mono- or di-esters of oxalic acid, and mixtures thereof. In another example, the 1,2-dioxygenated organic compound comprises glycolic acid, esters of glycolic acid, oligomers of glycolic acid, oligomers of glycolic acid esters, or mixtures thereof. In yet another example, the 1,2-dioxygenated organic compound comprises glycolic acid, esters of glycolic acid, or mixtures thereof.

The glycolic acid may be obtained from any source known in the art such as, for example, from commercial sources. Glycolic acid is typically made by contacting aqueous solutions of formaldehyde with carbon monoxide in the presence of an acid catalyst under elevated pressures and temperatures. These reactions are referred to herein as the "hydrocarboxylation" of formaldehyde and are exemplified in U.S. Pat. Nos. 2,152,852; 2,153,064; 2,211,624; 2,211,625; and 3,948,977; and United Kingdom Patent No. 1,499,245.

Glycolic acid esters include, but are not limited to, methyl glycolate, mono- and di-esters of the reaction of glycolic acid with ethylene glycol, various oligomers of glycolic acid or glycolate esters, or mixtures thereof. Glycolate esters are formed by the reaction between glycolic acid, or one or more oligomers of glycolic acid, and an alcohol, a diol, or a polyol. Examples of glycolate esters are the glycolate esters of ethylene glycol, which can be a monoester, a diester, or a mixture of mono- and diesters of ethylene glycol reacted with glycolic acid. Glycolic acid oligomers are dimers, trimers, or low molecular weight polymers of glycolic acid or a glycolic acid ester typically having 2 to about 20 repeating units. More typically, the glycolic acid or glycolic acid ester oligomers can have 2 to about 6 repeating units.

More specifically, glycolic acid oligomers are the reaction products of glycolic acid with itself, particularly the linear or cyclic esters formed by a reaction between a carboxyl group of one molecule and the alcohol group of another molecule. Gycolic acid oligomers include, but are not limited to 2-(2-hydroxyacetoxy)acetic acid, 2-(2-(2-hydroxyacetoxy)acetoxy)acetic acid, and 1,4-dioxane-2,5-dione. Typically, glycolic acid oligomers with two to four glycolic acid repeating units will be present with glycolic acid at temperatures used for the reaction of ethylene glycol and glycolic acid. When ethylene glycol and glycolic acid react, they not only react with each other but also with glycolic acid oligomers, as well as with reaction products such as 2-hydroxyethyl 2-hydroxyacetate, to thereby form glycolate ester oligomers. Examples include, but are not limited to 2-hydroxyethyl 2-hydroxyacetate, ethane-1,2-diyl bis(2-hydroxyacetate), 2-(2-2-(hydroxyacetoxy)acetoxy)ethyl 2-hydroxyacetate, 2-(2-(2-(2-(hydroxyacetoxy)acetoxy)acetoxy)ethyl 2-hydroxyacetate, 2-(2-hydroxyethoxy)-2-oxoethyl 2-hydroxyacetate, 2-(2-(2-hydroxyethoxy)-2-oxoethoxy)-2-oxoethyl 2 hydroxyacetate, and 2-(2-(2-(2-hydroxyethoxy)-2-oxoethoxy)-2-oxoethoxy)-2-oxoethyl 2 hydroxyacetate.

The reactants fed to the hydrogenation reactor may contain water or be fed as an aqueous solution.

Desirably, the concentration of glycolic acid, or esters of glycolic acid, or a combination thereof, in the feed to the hydrogenation reactor is not particularly limited. The concentration of reactants, or for example the concentration of the combination of glycolic acid and esters of glycolic acid, can be at a concentration of at least 30 wt. %, or at least 45 wt. %, or at least 70 wt. %, or at least 80 wt. %, and up to 100 wt. %, or up to 95 wt. %, based on the weight of feed reactant composition.

The hydrogenation organometallic catalyst employed is desirably a homogenous catalyst, meaning that the catalyst is in the same phase as the reaction product mixture. Ideally, the catalyst solubilizes in the reaction mixture at reaction temperatures.

The hydrogenation catalyst may comprise any metal or combination of metals effective for the hydrogenation of esters to alcohols. Typical hydrogenation catalysts include, but are not limited to, at least one metal selected from Groups 8, 9, 10 of the Periodic Table of the Elements (1984 Revision by IUPAC), and copper. The term "metal", as used herein in the context of homogeneous hydrogenation catalysts, is understood to include metal compounds, salts, or complexes with organic or inorganic ligands, wherein the metal can be in any oxidation state.

Examples of homogeneous hydrogenation catalysts include Wilkinson's catalyst, tris(triphenylphosphine)chlororhodium(I) (J. Chem. Soc. A, 1966, 1711-1732), chloro[1,3-bis(2,6-di-1-propylphenyl)imidazole-2-ylidene]copper(I) (Org. Lett. 2003, 5, 2147-2420), chlorodihydrido[bis(2-di-1-propylphosphinoethyl)amine]iridium(III) (Organometallics, 2006, 25, 4113-4117), diacetato[(S)-(−)-2,2'-bis(diphenylphosphino)-1,1'-binaphthyl]ruthenium(II) (J. Am. Chem. Soc., 1988, 110, 629-631), and all the tetradentate ruthenium complexes disclosed in U.S. Pat. No. 7,763,758, incorporated herein fully by reference with respect to such catalysts and their method of manufacture and use, and tridentate pincer complexes of ruthenium as discussed in Angew. Chem. Int. Ed., 2006, 45, 1113-1115.

In a preferred embodiment, the homogenous hydrogenation catalyst composition comprises ruthenium atoms, and a tridentate phosphorous ligand. Desirably, the ligand comprises 1,1,1-tris(diarylphosphino-methyl)alkanes or 1,1,1-tris(dialkylphosphinomethyl)-alkanes or a combination thereof.

The source of ruthenium is not particularly limiting and can be any ruthenium compound that is soluble in an organic solvent or in the reaction product mixture. Some non-limiting examples of ruthenium compounds include ruthenium salts, hydride complexes, carbonyl compounds, halides, oxides, phosphine complexes, and mixtures thereof. Suitable ruthenium salts include ruthenium carboxylates and acetylacetonates. For example, the ruthenium compound can comprise the acetonylacetonate or diacetate salts of a ruthenium coordination compound with any of the tridentate ligands set forth herein.

The preferred tridentate ligand can comprise 1,1,1-tris(diaryl-phosphinomethyl)alkanes or 1,1,1-tris(dialkylphosphinomethyl)alkanes, or combinations thereof, having the formula (I):

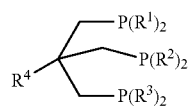

I wherein $R^4$ represents a substituted or unsubstituted, straight or branched chain alkyl radical having 1 to 40 carbon atoms or a substituted or unsubstituted cycloaliphatic radical containing 6 to 40 carbon atoms; and $R^1$, $R^2$, $R^3$ each independently may be a substituted or unsubstituted, straight or branched alkyl radical having 1 to 40 carbon atoms, an substituted or unsubstituted aryl radical having 6 to 20 carbon atoms, or a substituted or unsubstituted cycloaliphatic radical have 3 to 20 carbon atoms.

The alkyl radicals represented by $R^1$, $R^2$, $R^3$, and $R^4$ can be substituted with any group that does not interfere with the hydrogenation reaction such as, for example, hydroxyl, ether, halogen, sulfonic acid, carboxylic acid, and the like.

Examples of substituted and unsubstituted alkyl radicals include, but are not limited to, methyl, ethyl, cyanomethyl, nitromethyl, hydroxymethyl, trityloxymethyl, propionyloxymethyl, aminomethyl, carboxymethyl, methoxymethyl, ethoxymethyl, butoxymethyl, t-butoxymethyl, acetoxymethyl, chloromethyl, bromomethyl, iodomethyl, 6-hydroxyhexyl, 2,4-dichloro(n-butyl), 2-amino(isopropyl), n-propyl, isopropyl, isobutyl, n-butyl, tertiary butyl, pentyl, hexyl, 2-ethylhexyl, octyl, decyl, and various isomers thereof.

Examples of substituted and unsubstituted cycloaliphatic radicals include, but are not limited to, cyclopropyl, cyclobutyl, hydroxymethylcyclobutyl, cyclopentyl, cyclohexyl, cycloheptyl, 2-methylcyclopropyl, 4-methylcyclohexyl, 4-(isopropyl)-cyclohexylethyl or 2-methyl-cyclopropylpentyl, and the like.

Examples of substituted and unsubstituted aryl radicals are phenyl, napthyl, anthracenyl, 4-chlorophenyl, 2,6-dichlorophenyl, 2,5-dichlorophenyl, 3,4-dichlorophenyl, 3-chlorophenyl, 3-bromophenyl, 4-bromoindenyl, 3,4-dibromophenyl, 3,4-dibromonaphthyl, 3-chloro-4-fluorophenyl, 2-fluorophenyl, 4-hydroxyphenyl, 3-hydroxyphenyl, 2,4-dihydroxyphenyl, 4-cyanophenyl; 4-methylphenyl, 2,4-dimethylphenyl, 2-methylnaphthyl, 4-(isopropyl)phenyl, 4-ethylnaphthyl, 3-(n-propyl)phenyl, 2,6-dimethoxyphenyl, 4-methoxyphenyl, 3-ethoxyindenyl, 4-(iso-propoxy)phenyl, 4-(t-butoxy)phenyl, 3-ethoxy-4-methoxyphenyl, 3- or 4-trifluoromethylphenyl, 3,4-di(hydroxymethyl)phenyl, 2-(aminomethyl)phenyl, and 3-(methylsulfonylamino)naphthyl.

Exemplary tridentate phosphine ligands include, but are not limited to, 1,1,1 tris(diphenylphosphinomethyl)methane, 1,1,1-tris(diphenylphosphino-methyl)ethane, (2-(butoxymethyl)-2-((diphenylphosphino)methyl)propane-1,3-diyl)bis(diphenylphosphine), (2-(benzyloxymethyl)-2-((diphenylphosphino)-methyl)propane-1,3-diyl)bis(diphenylphosphine), 1,1,1-tris(diphenylphosphinomethyl)propane, 1,1,1-tris(diphenylphosphino-methyl)-butane, 1,1,1-tris(diphenylphosphinomethyl)-2,2-dimethylpropane, 1,1,1-tris(diphenylphosphinomethyl)cyclohexane, 1,1,1-tris(dicyclohexylphosphinomethyl)ethane, 1,1,1-tris(dimethylphosphinomethyl)ethane, 1,1,1-tris(diethylphosphinomethyl)ethane, or mixtures thereof. For example, the tridentate phosphine can comprise 1,1,1-tris(diphenylphosphinomethyl)ethane (also known as "triphos"), represented by formula (II), 1,1,1-tris(diethylphosphinomethyl)ethane, represented by formula (III), (2-(butoxymethyl)-2-((diphenylphosphino)methyl)propane-1,3-diyl)bis(diphenylphosphine), represented by formula (IV), (2-(benzyloxymethyl)-2-((diphenylphosphino)methyl)propane-1,3-diyl)bis(diphenylphosphine), represented by formula (V), or a poly(alkylenoxymethyl)-2-((diphenyl-phosphino)methyl)propane-1,3-diyl)bis(diphenylphosphine), represented by formula (VI):

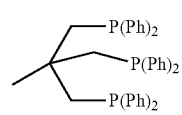

II

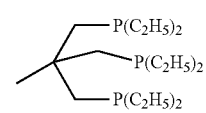

III

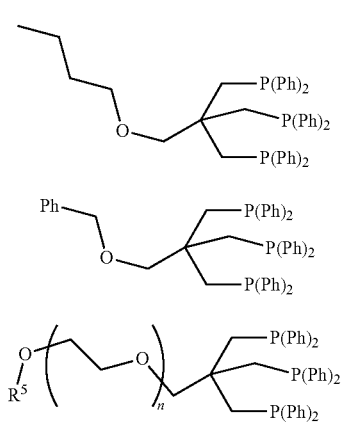

wherein n is 1 to 10 and $R^5$ is an alkyl or substituted alkyl group having 1 to 20 carbon atoms.

The concentration of the ruthenium and the tridentate ligand in the glycolic acid hydrogenation reaction mixture or product can vary over a wide range. In general, the metal concentrations (as the metal atoms, e.g. Ru) can be in the range of from about 1 part per million to about 10,000 parts per million based on the weight of the reaction product mixture excluding hydrogen.

Typically, a gram mole ligand:gram atom ruthenium ratio of at least 1:1 is maintained in the reaction mixture. More typically, the ratio ranges from 1:1 to 20:1 or 1:1 to 5:1.

As mentioned above, the catalyst composition may comprise ruthenium and a tridentate ligand such as 1,1,1-tris(diarylphosphino-methyl)alkanes and 1,1,1-tris(dialkylphosphinomethyl)alkanes. Some non-limiting examples of 1,1,1-tris(diarylphosphinomethyl)alkanes and 1,1,1-tris(dialkylphosphinomethyl)alkanes include 1,1,1-tris(diphenylphosphinomethyl)methane, 1,1,1-tris(diphenylphosphino-methyl)ethane, (2-(butoxymethyl)-2-((diphenylphosphino)methyl)propane-1,3-diyl)bis(diphenylphosphine), (2-(benzyloxymethyl)-2-((diphenylphosphino)-methyl)propane-1,3-diyl)bis(diphenylphosphine), 1,1,1-tris(diphenyl-phosphinomethyl)propane, 1,1,1-tris(diphenylphosphino-methyl)butane, 1,1,1-tris(diphenylphosphinomethyl)-2,2-dimethylpropane, 1,1,1-tris(diphenylphosphinomethyl)cyclohexane, 1,1,1-tris(dicyclohexylphosphinomethyl)ethane, 1,1,1-tris(dimethylphosphinomethyl)ethane, 1,1,1-tris(diethylphosphinomethyl)ethane, or mixtures thereof. For example, the catalyst composition can comprise a tridentate ligand comprising 1,1,1-tris(diphenylphosphinomethyl)ethane, (2-(butoxymethyl)-2-((diphenylphosphino)-methyl)propane-1,3-diyl)bis(diphenylphosphine), (2-(benzyloxymethyl)-2-((diphenylphosphino)methyl)propane-1,3-diyl)bis(diphenylphosphine), or mixtures thereof. In another embodiment, the tridentate ligand can comprise 1,1,1-tris(diphenylphosphinomethyl)ethane.

A desirable homogeneous catalyst includes ruthenium atoms and a tridentate ligand such as 1,1,1-tris(diarylphosphinomethyl)alkanes and 1,1,1-tris(dialkylphosphinomethyl)alkanes.

If desired, the catalyst components, metal, ligand, and promoter, can be dissolved in an organic solvent in the feed to the hydrogenation reactor, or added to a solvent within the hydrogenation reactor. The organic solvent may be selected from a wide variety of compounds, mixture of compounds, or materials that are liquid at the pressure at which the process is being operated. The main criteria for the solvent are that it can dissolve the catalyst components and reactants, and does not act as a poison to the catalyst. Suitable organic solvents include alcohols, ethers, hydrogenation reactants, and hydrogenation reaction products. Specific examples of suitable organic solvents include methanol, ethanol, propanol, butanol, isobutanol, isopropanol, ethylene glycol-neopentyl glycol, 2-ethylhexanol, diethylene glycol, triethylene glycol, glycerol, hexanol, octanol, methoxy ethanol, diisopropyl ether, dipropyl ether, xylene, toluene, benzene, or any other aromatic solvents, and mixtures thereof. Particularly suitable solvents include methanol, ethylene glycol, 2-ethylhexanol, hexanol, octanol, and mixtures thereof.

No special or unusual techniques are needed for preparing the catalyst systems, although in order to obtain a catalyst of high activity, it is preferred that manipulations of the ruthenium and phosphorus ligand components be carried out under an inert atmosphere, e.g., nitrogen, argon and the like. The desired quantities of a suitable ruthenium compound and ligand can be charged to the reactor in a suitable solvent. The sequence in which the various catalyst components or reactants are charged to the reactor can vary.

The hydrogen feed to the hydrogenation reactor can contain hydrogen in an amount of at least 60 mole %, or at least 70 mole %, or at least 95 mole %, or at least 99 mole % hydrogen.

Hydrogen pressure influences the outcome of the hydrogenation reaction. Lower pressures typically result in a slower rate of reaction. Suitable hydrogen pressure is in the range of at least 1 bara, or at least 20 bara, or at least 50 bara, and up to 300 bara, or up to 200 bara, or up to 150 bara.

The reactants, hydrogen, and catalyst can be fed to the hydrogenation reactor as single feed stream or with multiple feeds. The multiple feeds can be individual feed lines, with one feed line containing the fresh feed of reactants, another feed line containing the catalyst fed neat or solubilized in reactants, another optional feed containing recycled catalyst, another optional feed containing recycled ethylene glycol, and another feed for hydrogen, or any one of these feed lines can be combined, such as the catalyst and reactant feed in one line and hydrogen in a separate feed line. The feed lines may contain one or more of each of these constituents of the reaction mixture but in differing molar ratios to each other.

The reactants, catalyst, and hydrogen may be fed continuously, semi-continuously, or batch-wise. In addition, one or more reactants may be introduced at different locations in the reaction zone. The process of the present invention may be conducted under continuous, semi continuous, and batch modes of operation and may utilize a variety of equipment in the reaction zone. In a continuous mode, at least one of the reactants is introduced and at least a portion of the reaction product mixture is withdrawn simultaneously in an uninterrupted manner. A continuous mode can have interruptions in the continuity of the process due to, for example, start up, reactor maintenance, or scheduled shut down periods. Alternatively, the hydrogenation reaction can be conducted in a batch mode wherein all the reactants are added to the hydrogenation reactor and then processed according to a predetermined course of reaction during which no reactants are fed into the reaction zone during the course of the reaction with a simultaneous withdrawal of reaction product mixture, although the withdrawal of volatiles or a sweep of hydrogen is allowed within a batch mode. Alternatively, the reaction can proceed in a semicontinuous mode where some of the reactants are charged at the beginning of the process and the remaining reactants are fed continuously as the reaction progresses. Alternatively, a semi-continuous process may also include a process similar to a batch process in which all the reactants are added at the beginning of the process except that one or more of the products other than volatiles or hydrogen are removed continuously as the reaction progresses.

The hydrogenation reaction is conducted in the liquid phase using known processes. Typically, the reactants are contacted with hydrogen under pressure in the presence of a catalyst effective for hydrogenation at temperatures from about 100° C. to about 300° C. Additional examples of temperatures ranges are from at least 125° C., or at least 150° C., or at least 180° C., or at least 200° C., or at least 225° C., and up to about 300° C., or up to about 285° C.

The hydrogenation reaction is conducted for a period of time sufficient to produce ethylene glycol. Persons having ordinary skill in the art will understand that reaction time will be dependent, in part, upon factors such as temperature, pressure, catalyst concentration, nature and proportion of starting materials, and the like. The reaction time will typically be within the range of from about one-half to about 200 hours or more. For example, the reaction time can be from about one to about 10 hours.

Examples of suitable reactor types include, but are not limited to, stirred tank, continuous stirred tank, and tubular reactors. Any of the known hydrogenation reactor designs or configurations may be used for the hydrogenation reaction to produce the glycolic acid hydrogenation product. For example, the process may be conducted in a batchwise manner in an autoclave by contacting the glycolic acid with hydrogen in the presence of the catalyst compositions described herein. It will be apparent to those skilled in the art that other reactor schemes may be used with this invention. For example, the hydrogenation reaction can be conducted in a plurality of reaction zones, in series, in parallel, or it may be conducted batchwise or continuously in a tubular plug flow reaction zone or series of such zones with recycle of unconsumed feed substrate materials if required. The reaction steps may be carried out by the incremental addition of one of the feed substrate materials to the other. Also, the reaction steps can be combined by the joint addition of the feed substrate materials.

The reaction product mixture is the resulting mixture obtained by contacting hydrogen with the reactants in the presence of the homogeneous organometallic catalyst under reaction conditions effective to hydrogenate at least a portion of the reactants to produce ethylene glycol. The reaction product mixture is a liquid under the operating conditions, and desirably a liquid at 1 atmosphere and 25° C. The reaction product mixture is discharged from the hydrogenation reaction as a liquid or treated within the hydrogenation reactor in the liquid phase. The reaction product mixture typically comprises one or more of ethylene glycol, unreacted glycolic acid reactants or derivatives thereof (or oxalic acid if used as a reactant) if any remains unconverted, water, the homogeneous organometallic catalyst composition, and by-products.

The hydrogenation reaction results in the formation of ethylene glycol and by-products. The by-products include diol by-products, tetrol by-products, and glycolaldehyde acetal by-products. In addition to by-products, the homogeneous catalyst, and ethylene glycol, the reaction mixture may contain unreacted reactants and water.

The reaction product mixture can comprise ethylene glycol present in an amount of from at least 10 wt. %, or at least 20 wt. %, or at least 30 wt. %, or at least 40 wt. %, or at least 50 wt. %, or at least 60 wt. %, or at least 70 wt. %, or at least 80 wt. %, or at least 85 wt. %, or at least 90 wt. %, or at least 92 wt. %, or at least 95 wt. %, or at least 97 wt. %, or at least 98 wt. %, and in each case up to 99.9 wt. % based on the weight of the reaction product mixture.

The concentration of water in the reaction product mixture can be at least 0.1 wt. %, or at least 0.5 wt. %, or at least 1 wt. %, or at least 3 wt. %, or at least 5 wt. %, or at least 10 wt. %, or at least 20 wt. %, and in each case up to 50 wt. %, or up to 40 wt. %, or up to 30 wt. %, or up to 20 wt. %, or up to 15 wt. %, or up to 10 wt. %, based on the weight of the reaction product mixture.

Unreacted reactants can be present in an amount of at least 0.1 wt. %, or at least 0.5 wt. %, or at least 1 wt. %, or at least 3 wt. %, and in each case up to 30 wt. %, or up to 25 wt. %, or up to 20 wt. %, or up to 15 wt. %, or up to 10 wt. %, or up to 8 wt. %, or up to 5 wt. %, based on the weight of the reaction product mixture.

An advantage of the invention is that the rate of forming at least one of the by-products, in addition to the corresponding amount already present in the reaction product mixture, is reduced. The carbon monoxide passivation activity is unexpected since it is known that carbonylated triphos ruthenium complexes are active catalysts for hydrogenating glycolate esters to EG. The glycolate salt of the cationic dicarbonyl hydride complex, $[(Triphos)Ru(CO)_2H]^+$, for example can convert glycolate esters to EG in excess of 99% conversion and in excess of 99% selectivity.

Treatment of the homogeneous catalyst with the carbon monoxide gas composition is an effective method for minimizing the formation of additional by-products, especially by-product diols, once the reaction product mixture is discharged from the hydrogenation reactor or after the hydrogenation reaction is discontinued. If the reaction product mixture remains in the hydrogenation reactor such as in a batch process, the hydrogenation reaction is deemed discontinued when reaction conditions sufficient to hydrogenate the reactants are discontinued, such as by shutting off the flow of hydrogen or cooling the reaction product mixture within the hydrogenation reactor to a temperature below the hydrogenation temperature; e.g. below 100° C.

Once having discontinued the hydrogenation reaction or having discharged the reaction product mixture as an effluent, the reaction product mixture is contacted with a gaseous carbon monoxide composition. The carbon monoxide acts to passivate the homogeneous catalyst in the reaction product mixture to reduce the amount of by-product formation that is in addition to the by-product concentration already present in the reaction product mixture. The process of the invention is particularly well suited for suppressing the formation of additional by-products after contacting the reaction product mixture with the carbon monoxide gas composition. The carbon monoxide gas composition desirably contacts the reaction product mixture after discontinuing the hydrogenation reaction or in the hydrogenation reactor effluent that is subjected to further purification.

The carbon monoxide gas composition desirably contains at least 1 mole %, or at least 2 mole %, or at least 3 mole %, or at least 5 mole %, or at least 10 mole %, or at least 20 mole %, or at least 30 mole %, or at least 40 mole %, or at least 50 mole %, or at least 60 mole %, or at least 70 mole %, or at least 80 mole %, or at least 90 mole %, or at least 95 mole %, or at least 98 mole % carbon monoxide based on the moles of the gaseous carbon monoxide composition.

The reaction product mixture containing the homogeneous catalyst along with ethylene glycol is contacted with a flow of a gaseous carbon monoxide composition. The point of contact is upon or after discharge from the hydrogenation reactor; or inside the hydrogenation reactor, preferably after the hydrogenation reaction is discontinued, and more desirably at of after discharge of the reaction product mixture from the hydrogenation vessel, especially if the process is continuous.

For example, the gaseous carbon monoxide composition may be fed at the discharge port of the hydrogenation reactor vessel or to a location between the hydrogenation reactor and the first purification apparatus for separating at least a portion of one of the ingredients from the reaction product mixture, such as a distillation apparatus. The gaseous carbon monoxide composition may be fed to the first purification apparatus, such as a distillation apparatus. The gaseous carbon monoxide composition may be fed to the second purification apparatus, such as a distillation column. The gaseous carbon monoxide composition may be fed to a location between the first and second purification apparatus, such as to a point between two distillation columns. The gaseous carbon monoxide composition may be fed to the liquid bottoms of a purification apparatus, such as a distillation apparatus. The gaseous carbon monoxide composition may be fed to a location between a first purification apparatus and a vessel used at least in part to passivate the homogeneous catalyst, or directly to such vessel.

Since additional by-products tend to be formed under heat in non-reducing atmospheres, it is desirable to passivate the homogeneous catalyst at or before the first purification step in which at least a portion of one or more liquid ingredients in the liquid reaction product mixture is separated as a vapor from the liquid reaction product mixture. Thus, it is desirable to passivate the homogeneous catalyst (i) in the hydrogenation reactor, (ii) at any point between the hydrogenation reactor and the first purification vessel, (iii) or within the first purification vessel. For a continuous process, the passivation occurs along any of the latter two points (ii) or (iii).

At location (ii), the gaseous carbon monoxide composition can be fed to a pipe containing a flow of the reaction product mixture, to an in-line static mixer, to a pot and bubbled through the reaction product mixture, preferably through a sparge ring or dip tube that is optionally perforated, or into a pipe with an in-line mechanical mixer, or any other suitable device for contacting gas with a liquid and desirably creating maximum interfacial surface contact between the gas and liquid. Also, the gaseous carbon monoxide composition can be fed into a pipe containing a flow of the reaction product mixture feeding the first purification vessel.

At location (iii), the gaseous carbon monoxide composition can be fed directly into the first purification vessel, such as being introduced into a distillation apparatus as a gas feed. Although the carbon monoxide gas composition can be fed into the distillation apparatus at any location, to ensure contact with the homogeneous catalyst in the reaction product mixture, it is desired to feed the gas stream into the liquid reaction product mixture within the distillation apparatus. In the case of a distillation column operated to generate a distillate vapor rich in concentration of ethylene glycol relative to the concentration of the reaction product mixture feed to the distillation apparatus, and a bottoms liquid product rich in the concentration of homogeneous catalyst relative to the concentration of homogeneous catalyst in the reaction product mixture feed to the distillation apparatus, it is desirable to feed the gaseous carbon monoxide stream into the liquid bottoms. This can be accomplished with a pipe submerged in the liquid bottoms, or through a sparge ring submerged in the liquid bottoms, or at any point within the recirculation loop for heating the reaction product mixture (e.g. a reboiler loop). The point of entry in the liquid bottoms is not limited but should desirably be close to the bottom or within the recirculation loop heating the reaction product mixture to provide greater contact residence time between the gas bubbles and liquid phase. The use of a sparge ring has the additional advantage of greater gas dispersion in the liquid phase.

The partial pressure of carbon monoxide contacting the liquid reaction product mixture is at least 0.01 bara, or at least 0.1 bara, or at least 0.9 bara, or at least 1.0 bara, or at least 1.1 bara, or at least 2 bara, or at least 5 bara, or at least 8 bara, or at least 10 bara, or at least 11 bara, or at least 15 bara, or at least 20 bara, or at least 30 bara, or at least 40 bara, or at least 50 bara, or at least 60 bara, or at least 70 bara, or at least 90 bara, or at least 100 bara, or at least 150 bara, and up to 3000 bara, or up to 2000 bara, or up to 1500 bara, or up to 1000 bara, or up to 750 bara, or up to 500 bara, or up to 300 bara, or up to 150 bara, or up to 100 bara. Carbon monoxide partial pressures as low as 0.1 bara are effective to suppress the formation of by-product diols and by-product tetrols.

By-product diol, and optionally by-product tetrol, formation can be suppressed and even avoided by passivating the homogeneous catalyst, such as the ruthenium catalysts mentioned above, with 1 bara of CO partial pressure or less. Thus, bubbling CO through the liquid bottoms of a distillation column for separating ethylene glycol, or entraining CO in the feed at any point at or after discharge of the reaction product mixture from the hydrogenation reactor, is effective to suppress by-product diol, and optionally by-product tetrols, formation. However, by-product glycolaldehyde acetals still form at pressures of about 1 bara or less. The rate of by-product glycolaldehyde acetal formation can be significantly reduced by elevating the CO partial pressure to above 1 bara, such as greater than 5 bara, or greater than 8 bara, or at least 10 bara, or at least 11 bara, and can be suppressed completely when 70 bara partial CO or more is employed. Increasing the CO pressure above atmospheric during distillation, however, inevitably raises the boiling point of the EG product. Hence, where it is desired to suppress by-product glycoaldehye acetal formation, one may first pressurize the distillation chamber, containing the reaction product mixture, with CO in order to passivate the homogeneous catalyst, vent the distillation chamber down to atmospheric or sub-atmospheric pressure, and while venting or upon completion of venting, heat the reaction product mixture in the base of the distillation apparatus to commence distillation of ethylene glycol, and thereby allow for more facile distillation while reducing the rate of glycolaldehyde acetal formation. Alternatively, to provide for a continuous distillation mode, high pressure CO gas can be fed into any pipe or vessel between the hydrogenation reactor and the distillation column, and vented prior to entry into the column or vented inside the column. Alternatively, one may merely operate the column in a continuous mode at high pressure and elevate the heat energy input to vaporize ethylene glycol.

The temperature of the reaction product mixture that is in contact with the gaseous carbon monoxide composition, whether at the initial point of contact or thereafter, is at least 50° C., or at least 100° C., or at least 120° C., or at least 140° C., or at least 150° C. Desirably, the temperature of the reaction product mixture that is in contact with the gaseous carbon monoxide composition, whether at the initial point of contact or thereafter such as in a distillation column, can also be near or above the lowest operating temperature of liquid in the base of a distillation apparatus that is effective to separate from the liquid reaction product mixture at least 50 wt. % of 1,2-diol as a vapor that is present in the liquid reaction product mixture, prior to entry into the distillation apparatus, within two hours. By "near" is meant that the temperature of reaction product mixture contacting the carbon monoxide gas composition can be exactly the same as the lowest temperature in the base of a distillation apparatus or within 25° C. less than the lowest temperature of the liquid in the base of the distillation apparatus. The liquid at the base of the distillation apparatus is the liquid present within the base of the column and anywhere through the circulation loop feeding the base of the column including within the heat energy source (e.g. reboiler and/or heat exchanger) and the feed to the heat energy source.

The residence time of carbon monoxide gas with the reaction product mixture is effective at reducing the rate of diol formation above the diol content already present in the reaction product mixture. Although complete by-product diol suppression is not necessary, it is desired to employ a residence time which minimizes the rate of by-product diol formation so as to reduce the mass of by-product diol that must be then separated from ethylene glycol. Adequate residence times will also vary with the CO partial pressure. The higher pressures require shorter residence times to achieve the same level of by-product diol suppression. An additional advantage of higher CO partial pressures is the suppression of by-product glycolaldehyde acetal compounds. Suitable residence times can be at least 3 seconds, or at least 1 second, or at least 0.1 second, or at least 0.01 second, and up to 1 hour, or up to 30 minutes, or up to 15 minutes, or up to 10 minutes, or up to 5 minutes, or up to 3 minutes, or up to 1 minute. Those of skill can adjust the residence time and the CO partial pressure to achieve the desired level of by-product suppression.

The method for separating ethylene glycol from the reaction product mixture is not limited. The homogeneous catalyst separated from ethylene glycol can be recycled back to the hydrogenation reactor. Examples of separation techniques that can be employed to separate ethylene glycol from the reaction product mixture to form a liquid catalyst rich stream include vapor stripping, flash evaporation or distillation, fractionation distillation, vacuum distillation, and liquid-liquid extraction. The catalyst rich stream depleted in concentration of ethylene glycol relative to the concentration of ethylene glycol in the reaction product mixture feeding the separation apparatus, can be returned directly to the hydrogenation reactor for use or can be further treated before reuse in the hydrogenation reactor. The catalyst rich composition can be diluted with an alcohol solvent such as methanol or the reaction product such as ethylene glycol and reused. As another alternative or in addition, the catalyst rich composition can be further distilled to remove any remaining by-products which did not carry overhead with ethylene glycol in the first ethylene glycol distillation step. It is understood that the separation process described above can be combined with any of the various embodiments of the inventive process described herein.

The reaction product mixture may contain by-products. As mentioned above, by-products are produced in the course of the hydrogenation reaction, and by passivating the homogeneous catalyst after the reaction product mixture has undergone hydrogenation, further formation of by-products can be suppressed. The amount of by-product formation stated below refers to the amount of additional by-product formed after subjecting the reaction product mixture to hydrogenation conditions. Thus, the term "supplemental" amount refers to the additional amount of by-product formed after hydrogenation is complete. To determine the amount of additional by-product formed, one may measure the amount of by-product present in the reaction product mixture upon conclusion of the hydrogenation reaction or upon discharge from the hydrogenation vessel and then again measure the amount of by-products contained in the effluent streams after the first purification step, e.g. in an overhead distillate and in the liquid bottoms of a distillation reactor.

One of the by-products can be by-product diols in a supplemental amount of less than 0.01 mole %, or less than 0.009 mole %, or less than 0.008 mole %, or less than 0.007 mole %, or less than 0.006 mole %, or less than 0.005 mole %, or less than 0.004 mole %, or less than 0.003 mole %, or less than 0.002 mole %, or less than 0.001 mole %, in each case based on the total moles of all compounds in the reaction product mixture. The reaction product mixture may contain by-product diols, if present at all, in a supplemental amount of 0.000 mole % by-product diols or less, meaning that if any by-product diols are detected, they are present below three significant digits to the right of the decimal (with this convention applied throughout).

The reaction product mixture may also contain by-product tetrols. If present, they are desirably present in a supplemental amount of less than 0.02 mole %, or no more than 0.015 mole %, or no more than 0.012 mole %, or no more than 0.01 mole %, or no more than 0.009 mole %, or no more than 0.007 mole %, or no more than 0.005 mole %, or no more than 0.003 mole %, or no more than 0.002 mole %, or no more than 0.001 mole %, or no more than 0.000 mole %, or no more than 0.0005 mole %, or no more than 0.0000 mole %, each based on the total moles of all compounds in the reaction product mixture.

The reaction product mixture may also contain glycoaldehyde acetal compounds. If present, the supplemental amount is desirably less than 0.01 mole %, or no more than 0.009 mole %, or no more than 0.008 mole %, or no more than 0.007 mole %, or no more than 0.006 mole %, or no more than 0.005 mole %, or no more than 0.004 mole %, or no more than 0.003 mole %, or no more than 0.002 mole %, or no more than 0.001 mole %, or no more than 0.000 mole %, each based on the total moles of all compounds in the reaction product mixture.

EXAMPLES

Description of Synthetic Product Feed A

A liquid consisting entirely of ethylene glycol was used to represent a 100% conversion feed from glycolic acid. The ethylene glycol was pure at 99.997% ethylene glycol, containing 0.002 to 0.003 mole % by-product diols.

Description of Synthetic Product Feed B

The substrate used in several of the reactions described below was prepared by stirring a mixture of 1.68 Kg of ethylene glycol, 465.6 g of the diester of ethylene glycol and two equivalents of glycolic acid and 256.8 g of deionized water for one hour. The resulting mixture was determined to contain 84.6 mole % ethylene glycol equivalents by GC.

Synthesis $(Ph_3P)_2Ru(OAc)_2$

A 500 mL round bottom Schlenk flask equipped with a stir bar was charged with 10.525 g $(PPh_3)_3RuCl_2$ and 9.004 g sodium acetate trihydrate and fitted with a condenser capped by a septum. The flask was evacuated and refilled with Ar, then 250 mL of tert-butanol was poured in the top of the condenser under a flow of argon. The septum was replaced by an oil bubbler equipped with an argon inlet adaptor, the valve on the Schlenk flask was closed, and an argon flow was initiated through the upper inlet. The flask was immersed in an oil bath and heated at 100° C. to reflux the mixture for 90 minutes, during which time the color changed from red to orange, after which the mixture was cooled overnight. The product was isolated by pouring the mixture (in air) into a 150 mL medium porosity, glass frit, suction filter funnel, using 200 mL water to complete the transfer, and 300 mL additional water to wash away the bulk of the sodium acetate and sodium chloride, stirring the crystals as needed to ensure good mixing. The red-brown product was further washed with 200 mL (fresh) diethyl ether, another 150 mL water (to remove some white crystals, presumed to be residual sodium acetate), 130 mL ether, 25 mL 80/20 MeOH/water (in which the product has significant solubility, and for which a new collection flask was put in place) and finally another 70 mL ether. The solid was air-dried then dried in vacuo overnight to obtain 6.903 g (85%) red-brown solid, >95% pure by $^{31}$P NMR, evincing a single peak at 63.324 ppm ($CD_2Cl_2$ solvent) relative to an internal standard of $H_3PO_4$ in $D_2O$.

Synthesis of (Triphos)Ru(OAc)$_2$

A 250 mL round bottom Schlenk flask equipped with a stir bar was charged with 2.00 g ($PPh_3$)$_2$Ru(OAc)$_2$ (1 eq) and 1.77 g Triphos (Aldrich, 1.03 eq) and fitted with a condenser capped by a septum. The flask was evacuated and refilled with argon, then 100 mL of de-oxygenated anhydrous toluene was added via syringe from the top of the condenser under argon. The septum was replaced by an oil bubbler equipped with an argon inlet adaptor, the valve on the Schlenk flask was closed, and an argon flow was initiated through the upper inlet. The mixture was stirred at 25-35° C. for 1 hour, during which time the orange starting material dissolved and a yellow product precipitated. The mixture was stirred overnight to complete reaction, then 40 mL (fresh) diethyl ether were added and the product isolated by suction filtration (in air) using a 60 mL medium porosity glass frit. The solid was washed with 2×35 mL diethyl ether, and then 2×80 mL heptanes and first air-dried and then dried further in vacuo to obtain the product as a yellow crystalline solid (2.06 g, 91%). $^{31}$P NMR in acetic acid-d4 gave one main peak (99.5%) at 40.899, relative to $H_3PO_4$ in $D_2O$.

Synthesis of (Triphos)Ru(CO)$_2$

The Triphos ligand (5.0 g, 8.0 mmol) and ruthenium dodecacarbonyl (1.71 g, 2.67 mmol) were added to a 250 mL Schlenk flask as solids. 150 mL of degassed, anhydrous toluene was added via cannula to give an orange suspension. The flask was then fitted with a reflux condenser and placed in an oil bath heated to 130° C. (all solids dissolved upon warming and the solution color changed from orange to deep red). After one hour at reflux an orange precipitate formed. The heating was continued overnight (16 h) to give a light orange precipitate suspended in an orange supernatant. 50 mL of degassed hexanes were then added to the reaction flask via cannula and the precipitate collected under argon on a filter stick, washed with 2×20 mL of hexanes and dried in vacuo. The product was collected as a moderately air sensitive yellow-orange microcrystalline powder (4.07 g, 65%). $^{31}$P NMR (121.47 MHz, $CD_2Cl_2$): δ 27.9 (s).

Synthesis of [(Triphos)RuH(CO)$_2$]O$_2$CCH$_2$OH (Triphos)Ru(CO)$_2$ (1.27 g, 1.62 mmol) was dissolved in 40 mL of dry, degassed dichloromethane to give an orange solution. Solid glycolic acid (0.246 g, 3.24 mmol) was added under a flow of argon and the mixture stirred for five hours to give a near colorless solution. The solvent was then removed in vacuo to give the product as an off-white solid (0.95 g, 68%). ES/MS (water:methanol): m/z=783.1 [(Triphos)Ru(CO)$_2$H]$^+$. $^{31}$P NMR (121.47 MHz, $CD_2Cl_2$): δ 18.4 (d, J=27.9 Hz, 2P); 7.3 (t, J=27.9 Hz, 1P). $^1$H NMR (300 MHz, $CD_2Cl_2$): δ 7.6-6.6 (m, 30H, Ph); 4.0 (s, 2H, $O_2CCH_2OH$); 2.68 (d, J=9.0 Hz, 2H, $CH_2$); 2.52-2.42 (m, 4H, $CH_2$); 1.80 (q, 3H, $CH_3$); −6.7 (dt, J=64.0, 15.0 Hz, 1H, Ru—H).

Example 1

Heating of Synthetic Product Feed A in the Presence of a Ruthenium Precatalyst Under a 70 Bara Carbon Monoxide Atmosphere A 100 mL autoclave was charged with a solution of (Triphos)Ru(OAc)$_2$ (0.0523 g) in 80.28 g of synthetic product feed A. A sample was then taken and analyzed by GC. The autoclave was then sealed, flushed three times with 15 bara nitrogen, then three times with 21 bara carbon monoxide. Stirring (1000 rpm) was then commenced and the reactor pressurized with 34 bara CO, heated to 190° C. then pressurized up to 70 bara with CO. The reactor contents were sampled at various intervals after the autoclave temperature reached 190° C. The pressure of the autoclave was maintained at 70 bara throughout the run. After eight hours at 190° C., the reactor was cooled to room temperature and depressurized. The reactor samples were analyzed by GC and the mole percent byproduct composition of the final product summarized in Table 1. This example demonstrates that essentially no byproducts are formed when 70 bara CO is used as the reaction gas.

Example 2

Heating of Synthetic Product Feed A in the Presence of a Ruthenium Precatalyst Under a 11 Bara Carbon Monoxide Atmosphere A 100 mL autoclave was charged with a solution of (Triphos)Ru(OAc)$_2$ (0.0503 g) in 80.08 g of synthetic product feed A. A sample was then taken and analyzed by GC. The autoclave was then sealed, flushed three times with 11 bara nitrogen, then three times with 11 bara carbon monoxide. Stirring (1000 rpm) was then commenced and the reactor pressurized with 11 bara CO and then heated to 190° C. The reactor contents were sampled at various intervals after the autoclave temperature reached 190° C. The pressure of the autoclave was maintained at 11 bara throughout the run. After eight hours at 190° C., the reactor was cooled to room temperature and depressurized. The reactor samples were analyzed by GC and the mole percent byproduct composition of the final product summarized in Table 1. This example demonstrates that no by-product diols or by-product tetrols are formed under these autoclave conditions. Glycolaldehydes are formed but at insignificant amounts.

Comparative Example 1

Heating of Synthetic Product Feed A in the Presence of a Ruthenium Precatalyst Under a 11 Bara Hydrogen Atmosphere The reaction in this example was carried out as described in Example 2 except that hydrogen was used in place of carbon monoxide. The amount of synthetic product feed A charged to the autoclave was 80.14 g and the amount of (Triphos)Ru(OAc)$_2$ was 0.0513 g. The reactor samples were analyzed by GC and the mole percent byproduct composition of the final product summarized in Table 1. This example demonstrates that 11 bara of hydrogen pressure is adequate for minimizing glycolaldehydes but forms considerably more by-product diols and by-product tetrols than the previous examples. The amount of by-product diols, for example, is more than ten times higher than the corresponding CO experiment (Example 2).

Comparative Example 2

Heating of Synthetic Product Feed A in the Presence of a Ruthenium Precatalyst Under a 11 Bara Nitrogen Atmosphere The reaction in this example was carried out as described in Example 2 except that nitrogen was used in place of carbon monoxide. The amount of synthetic product feed A charged to the autoclave was 80.14 g and the amount of (Triphos)Ru(OAc)$_2$ was 0.053 g. The reactor samples were analyzed by GC and the mole percent byproduct composition of the final product summarized in Table 1. This example demonstrates that 11 bara of nitrogen pressure is insufficient for preventing byproduct formation. By-product diols are twenty five times higher in concentration than observed in Example 2 and the glycolaldehydes and by-product tetrols are markedly higher than all of the previous examples.

TABLE 1

| Example | Gas Type | Pressure | mol % Glycolaldehyde acetals | mol % By-product diols | By-product diol Increase Relative to Ex. 2 | mol % By-product tetrols |
|---|---|---|---|---|---|---|
| Example 1 | CO | 70 bara | 0.006% | 0.003% | n/a | 0.000% |
| Example 2 | CO | 11 bara | 0.01% | 0.002% | 1 | 0.000% |
| Comp. Ex. 1 | H$_2$ | 11 bara | 0.03% | 0.026% | 13 | 0.024% |
| Comp. Ex. 2 | N$_2$ | 11 bara | 0.113% | 0.051% | 25 | 0.079% |

Example 3

Heating of Synthetic Product Feed A in the Presence of a Ruthenium Precatalyst Under a 1 Bara Carbon Monoxide Atmosphere The reaction in this example was carried out as described in Example 2 except that the autoclave was not pressurized after the last CO flush. Thus, the reactor pressure was approximately 1 bara prior to heat up and sampling. The amount of synthetic product feed A charged to the autoclave was 80.09 g and the amount of (Triphos)Ru(OAc)$_2$ was 0.0511 g. The reactor samples were analyzed by GC and the mole percent byproduct composition of the final product summarized in Table 2. This example demonstrates that 1 bara CO is quite effective for inhibiting formation of glycolaldehydes, by-product diols and by-product tetrols.

Comparative Example 3

Heating of Synthetic Product Feed A in the Presence of a Ruthenium Precatalyst Under a 1 Bara Hydrogen Atmosphere The reaction in this example was carried out as described in Example 3 except that hydrogen was used in place of carbon monoxide. The amount of synthetic product feed A charged to the autoclave was 80.18 g and the amount of (Triphos)Ru(OAc)$_2$ was 0.0504 g. The reactor samples were analyzed by GC and the mole percent byproduct composition of the final product summarized in Table 2. This example demonstrates that 1 bara of hydrogen pressure is insufficient for preventing the formation of all three major byproducts. The concentration of by-product diols, for example, is more than twenty five times higher than that observed in Example 3.

Comparative Example 4

Heating of Synthetic Product Feed A in the Presence of a Ruthenium Precatalyst Under a 1 Bara Nitrogen Atmosphere The reaction in this example was carried out as described in Example 3 except that nitrogen was used in place of carbon monoxide. The amount of synthetic product feed A charged to the autoclave was 80.2 g and the amount of (Triphos)Ru(OAc)$_2$ was 0.0551 g. The reactor samples were analyzed by GC and the mole percent byproduct composition of the final product summarized in Table 2. This example demonstrates that 1 bara of nitrogen pressure is ineffective for byproduct inhibition.

TABLE 2

| Example | Gas Type | Pressure | mol % Glycolaldehyde acetals | mol % By-product diols | By-product diols relative to Ex. 3 | mol % By-product tetrols |
|---|---|---|---|---|---|---|
| Example 3 | CO | 1 bara | 0.000% | 0.002% | 1 | 0.000% |
| Comp. Ex. 3 | H$_2$ | 1 bara | 0.038% | 0.053% | 27 | 0.051% |
| Comp. Ex. 4 | N$_2$ | 1 bara | 0.064% | 0.058% | 29 | 0.064% |

Example 4

Heating of Synthetic Product Feed B in the Presence of a Ruthenium Precatalyst Under a 70 Bara Carbon Monoxide Atmosphere A 100 mL autoclave was charged with a solution of (Triphos)Ru(OAc)$_2$ (0.0532 g) in 80.09 g of synthetic product feed B and a sample taken and analyzed by GC. The autoclave was then sealed, flushed three times with 15 bara nitrogen, then three times with 21 bara carbon monoxide. Stirring (1000 rpm) was then commenced and the reactor pressurized with 34 bara CO, heated to 190° C. then pressurized up to 70 bara with CO. The reactor contents were sampled prior at various intervals after the autoclave temperature reached 190° C. The pressure of the autoclave was maintained at 70 bara throughout the run. After eight hours at 190° C., the reactor was cooled to room temperature and depressurized. The reactor samples were analyzed by GC and the mole percent byproduct composition of the final product summarized in Table 3. This example demonstrates that no byproducts are formed even after eight hours of heating when 70 bara of CO is used as the reaction gas.

Example 5

Heating of Synthetic Product Feed B in the Presence of a Ruthenium Precatalyst Under a 11 Bara Carbon Monoxide Atmosphere A 100 mL autoclave was charged with a solution of (Triphos)Ru(OAc)$_2$ (0.0502 g) in 80.11 g of synthetic product feed B and a sample taken and analyzed by GC. The autoclave was then sealed, flushed three times with 11 bara nitrogen, then three times with 11 bara carbon monoxide. Stirring (1000 rpm) was then commenced and the reactor pressurized with 11 bara CO and then heated to 190° C. The reactor contents were sampled at various intervals after the autoclave temperature reached 190° C. The pressure of the autoclave was maintained at 11 bara throughout the run. After eight hours at 190° C., the reactor was cooled to room temperature and depressurized. The reactor samples were analyzed by GC and the mole percent byproduct composition of the final product summarized in Table 3. This example demonstrates that essentially no by-product diols and by-product tetrols are formed when the feed is heated under a 11 bara CO atmosphere. Glycolaldehyde acetal levels reach approximately 0.05 mol %

Comparative Example 5

Heating of Synthetic Product Feed B in the Presence of a Ruthenium Precatalyst Under a 11 Bara Hydrogen Atmosphere The reaction in this example was carried out as described in Example 3 except that hydrogen was used in place of carbon monoxide. The amount of synthetic product feed B charged to the autoclave was 80.0 g and the amount of (Triphos)Ru(OAc)$_2$ was 0.0505 g. The reactor samples were analyzed by GC and the mole percent byproduct composition of the final product summarized in Table 3. This example demonstrates that 11 bara of hydrogen pressure is not as effective as the equivalent amount of carbon monoxide for suppressing byproduct formation. Glycolaldehyde acetal levels are lower than that of Example 5, however, by-product diols and by-product tetrols are significantly more abundant.

Comparative Example 6

Heating of Synthetic Product Feed B in the Presence of a Ruthenium Precatalyst Under a 11 Bara Nitrogen Atmosphere The reaction in this example was carried out as described in Example 3 except that nitrogen was used in place of carbon monoxide. The amount of synthetic product feed B charged to the autoclave was 80.03 g and the amount of (Triphos)Ru(OAc)$_2$ was 0.0503 g. The reactor samples were analyzed by GC and the mole percent byproduct composition of the final product summarized in Table 3. This example demonstrates that 11 bara of nitrogen pressure is not as effective as the equivalent amount of carbon monoxide for suppressing byproduct formation. The concentrations of all three main byproducts are significantly higher than those of Example 5.

TABLE 3

| Example | Gas Type | Pressure | mol % Glycolaldehyde acetals | mol % By-product diols | By-product diols Relative to Ex. 5 | mol % By-product tetrols |
|---|---|---|---|---|---|---|
| Example 4 | CO | 70 bara | 0.000 | 0.003 | n/a | 0.000 |
| Example 5 | CO | 11 bara | 0.047 | 0.001 | 1 | 0.000 |
| Comp. Ex. 5 | H$_2$ | 11 bara | 0.011 | 0.019 | 19 | 0.033 |
| Comp. Ex. 6 | N$_2$ | 11 bara | 0.164 | 0.022 | 22 | 0.04 |

Example 6

Heating of Synthetic Product Feed B in the Presence of a Ruthenium Precatalyst Under a 1 Bara Carbon Monoxide Atmosphere The reaction in this example was carried out as described in Example 5 except that the autoclave was not pressurized after the last CO flush. Thus, the reactor pressure was approximately 1 bara prior to heat up and sampling.

The amount of synthetic product feed B charged to the autoclave was 80.02 g and the amount of (Triphos)Ru(OAc)$_2$ was 0.0509 g. The reactor samples were analyzed by GC and the mole percent byproduct composition of the final product summarized in Table 4. This example demonstrates that although glycolaldehyde acetals form in about 0.2 mol %, the formation of by-product diols and by-product tetrols is effectively suppressed.

Comparative Example 7

Heating of Synthetic Product Feed B in the Presence of a Ruthenium Precatalyst Under a 1 Bara Hydrogen Atmosphere The reaction in this example was carried out as described in Example 6 except that hydrogen was used in place of carbon monoxide. The amount of synthetic product feed B charged to the autoclave was 80.01 g and the amount of (Triphos)Ru(OAc)$_2$ was 0.05 g. The reactor samples were analyzed by GC and the mole percent byproduct composition of the final product summarized in Table 4. This example demonstrates that 1 bara of hydrogen pressure is not as effective as the equivalent amount of carbon monoxide for suppressing by-product diol and by-product tetrol byproduct formation. Glycolaldehyde acetal levels are lower than those of Example 6, but the by-product diols and by-product tetrols are about four to five times more abundant.

Comparative Example 8

Heating of Synthetic Product Feed B in the Presence of a Ruthenium Precatalyst Under a 1 Bara Nitrogen Atmosphere The reaction in this example was carried out as described in Example 6 except that nitrogen was used in place of carbon monoxide. The amount of synthetic product feed B charged to the autoclave was 80.01 g and the amount of (Triphos)Ru(OAc)$_2$ was 0.05 g. The reactor samples were analyzed by GC and the mole percent byproduct composition of the final product summarized in Table 4. This example demonstrates that 1 bara of nitrogen pressure is not as effective as the equivalent amount of carbon monoxide for suppressing byproduct formation. Glycolaldehyde acetal levels are comparable to those of Example 6, but the by-product diols and by-product tetrols are about nine to ten times more abundant.

TABLE 4

| Example | Gas Type | Pressure | mol % Glycolaldehyde acetals | mol % By-product diols | By-product diols relative to Ex. 6 | mol % By-product tetrols |
|---|---|---|---|---|---|---|
| Example 6 | CO | 1 bara | 0.223 | 0.003 | 1 | 0.004 |

TABLE 4-continued

| Example | Gas Type | Pressure | mol % Glycolaldehyde acetals | mol % By-product diols | By-product diols relative to Ex. 6 | mol % By-product tetrols |
|---|---|---|---|---|---|---|
| Comp. Ex. 7 | $H_2$ | 1 bara | 0.095 | 0.011 | 3.7 | 0.022 |
| Comp. Ex. 8 | $N_2$ | 1 bara | 0.146 | 0.027 | 9 | 0.038 |

Example 7

Heating of Synthetic Product Feed B in the Presence of a Ruthenium Precatalyst Under a 0.1 Bara Carbon Monoxide Atmosphere The reaction in this example was carried out as described in Example 5 except that the reactor was pressurized to 7.9 bara with carbon monoxide followed by 63 bara of nitrogen. The reactor was stirred at 1000 rpm for thirty minutes then vented down to atmospheric pressure. Thus, the CO partial pressure of the reactor was calculated to be approximately 0.1 bara prior to heating and sampling. The amount of synthetic product feed B charged to the autoclave was 79.99 g and the amount of (Triphos)Ru(OAc)$_2$ was 0.05 g. The reactor samples were analyzed by GC and the mole percent byproduct composition of the final product summarized in Table 5. This example demonstrates that a CO partial pressure as low as 0.1 bara is sufficient for completely suppressing by-product diol and by-product tetrol formation. Glycolaldehyde acetal levels are comparable to those of Example 6.

Comparative Example 9

Heating of Synthetic Product Feed B in the Presence of a Ruthenium Precatalyst Under a 0.1 Bara Hydrogen Atmosphere The reaction in this example was carried out as described in Example 6 except that hydrogen was used in place of carbon monoxide. The amount of synthetic product feed B charged to the autoclave was 80.01 g and the amount of (Triphos)Ru(OAc)$_2$ was 0.05 g. The reactor samples were analyzed by GC and the mole percent byproduct composition of the final product summarized in Table 5. This example demonstrates that 0.1 bara hydrogen pressure does not adequately suppress the formation of by-product diols and by-product tetrols when compared to results described in Example 6. Glycolaldehyde acetal levels are comparable to those of Example 7 but the by-product diols and by-product tetrols are at least ten times as abundant.

TABLE 5

| Example | Gas Type | Pressure | mol % Glycolaldehyde acetals | mol % By-product diols | By-product diols relative to Ex. 6 | mol % By-product tetrols |
|---|---|---|---|---|---|---|
| Example 7 | CO | 0.1 bara | 0.18 | 0.002 | 1 | 0.000 |
| Comp. Ex. 9 | $H_2$ | 0.1 bara | 0.118 | 0.02 | 10 | 0.032 |

Example 8

Hydrogenation of a Glycolate Ester with a Carbonylated Triphos Ruthenium Catalyst A 300 mL stainless steel autoclave was charged with 0.08 g of [(Triphos)RuH(CO)$_2$]O$_2$CCH$_2$OH (i.e., the glycolate salt of the dicarbonyl hydride complex) and 200 g of a mixture of glycolate esters. The autoclave was then sealed, flushed three times with 200 psig nitrogen, pressurized to 1200 psig hydrogen, heated to 190° C., then pressurized to a total of 2400 psig with hydrogen (stirrer speed=1200 rpm). After 12 hours at 190° C., the reactor was cooled to room temperature, depressurized and the product decanted and submitted for analysis. GC analysis of the product indicated 99% conversion of the ester substrate to ethylene glycol in 99% selectivity. This example demonstrates that the dicarbonyl hydride complex is a suitable precatalyst for glycolate ester hydrogenation even though it is a carbonylated ruthenium complex.

What we claim is:

1. A process for making ethylene glycol comprising:
   (i) feeding reactants comprising 1,2-dioxygenated organic compounds, an organometallic homogeneous catalyst, and hydrogen to a hydrogenation reactor;
   (ii) conducting a hydrogenation reaction by reacting at least a portion of the reactants with hydrogen in the hydrogenation reactor and in the presence of the catalyst to produce a reaction product mixture comprising ethylene glycol and the catalyst;
   (iii) contacting the catalyst with a carbon monoxide gas composition containing at least 1 mole % carbon monoxide; and
   (iv) separating at least a portion of the ethylene glycol from the reaction product mixture.

2. The process of claim 1, wherein said reaction product mixture contains at least 70 wt. % ethylene glycol.

3. The process of claim 2, wherein said reaction product mixture contains at least 90 wt. % ethylene glycol.

4. The process of claim 2, wherein the carbon monoxide composition comprises at least 50 mole % carbon monoxide.

5. The process of claim 4, wherein the carbon monoxide composition comprises at least 90 mole % carbon monoxide.

6. The process of claim 1, comprising contacting the reaction product mixture with the carbon monoxide gas composition under a carbon monoxide partial pressure of at least 0.01 bara.

7. The process of claim 6, wherein the partial pressure of carbon monoxide contacting the reaction product mixture is at least 10 bara.

8. The process of claim 7, wherein the carbon monoxide partial pressure pressure is at least 50 bara.

9. The process of claim 8, wherein the temperature of the reaction product mixture that is in contact with carbon monoxide gas composition is at least 100° C.

10. The process of claim 8, wherein the temperature of the reaction product mixture that is in contact with carbon monoxide composition is at least 225° C.

11. The process of claim 8, wherein the temperature of the reaction product mixture that is in contact with carbon monoxide gas composition is near or above the lowest operating temperature of liquid in the base of a distillation apparatus effective to separate from the liquid reaction product mixture at least 50 wt. % of ethylene glycol as a vapor that is present in the liquid reaction product mixture prior to entering the distillation apparatus.

12. The process of claim 1, wherein the residence time of carbon monoxide with the reaction product mixture is effective to reducing the rate of by-product diol formation.

13. The process of claim 12, wherein the residence time of carbon monoxide with the reaction product mixture is 10 minutes or less.

14. The process of claim 1, wherein the (iii) separation is conducted in a distillation apparatus comprising a fractional distillation column and taking ethylene glycol as an overhead distillate.

15. The process of claim 1, wherein the carbon monoxide composition is fed into the base of the distillation apparatus.

16. The process of claim 1, wherein the carbon monoxide composition is contacted with the reaction product mixture after the hydrogenation reaction is discontinued or to the reaction product mixture discharged from the hydrogenation reactor and before the reaction product mixture is introduced into an apparatus for conducting the (iii) separation.

17. The process of claim 1, wherein the process is continuous.

18. The process of claim 1, wherein the homogeneous organometallic catalyst comprises ruthenium atoms and a tridentate phosphorous ligand.

19. The process of claim 1, wherein the reaction product mixture is contacted with said carbon monoxide gas composition, and the cumulative supplemental amount of 1,2-propanediol and 1,2-butanediol formed as diol by-products after first contact with said carbon monoxide gas composition is less than 0.01 mole % based on the weight of the reaction product mixture.

20. The process of claim 19, wherein the supplemental cumulative amount of 1,2-propanediol and 1,2-butanediol is less than 0.003 mole %.

21. The process of claim 1, wherein the reaction product mixture is contacted with said carbon monoxide gas composition, and the cumulative supplemental amount of by-product tetrols formed as by-product tetrols after first contact with said carbon monoxide gas composition is less than 0.01 mole % based on the weight of the reaction product mixture.

22. The process of claim 1, wherein the cumulative supplemental amount of tetrols formed as tetrols by-products after first contact with said carbon monoxide gas composition is less than 0.005 mole % based on the weight of the reaction product mixture.

23. The process of claim 1, wherein the reaction product mixture is contacted with said carbon monoxide gas composition, and the cumulative supplemental amount of glycolaldehyde acetal compounds formed as acetal by-products after first contact with said carbon monoxide gas composition is less than 0.01 mole % based on the weight of the reaction product mixture.

* * * * *